United States Patent
Filsouf

(10) Patent No.: US 7,475,695 B2
(45) Date of Patent: Jan. 13, 2009

(54) FLOSSING DEVICE WITH INTERNAL FLOSS FEED

(76) Inventor: Ehsan Filsouf, 8590 SW. 168th Ter., Miami, FL (US) 33157

( * ) Notice: Subject to any disclaimer, the term of this patent is extended or adjusted under 35 U.S.C. 154(b) by 0 days.

(21) Appl. No.: 11/858,232

(22) Filed: Sep. 20, 2007

(65) Prior Publication Data

US 2008/0006289 A1   Jan. 10, 2008

Related U.S. Application Data

(63) Continuation-in-part of application No. 10/846,575, filed on May 17, 2004, now abandoned.

(51) Int. Cl.
*A61C 15/00* (2006.01)

(52) U.S. Cl. .................................... 132/324

(58) Field of Classification Search .......... 132/322–327
See application file for complete search history.

(56) References Cited

U.S. PATENT DOCUMENTS

| 3,376,876 | A | 4/1968 | Wicklund |
| 3,421,524 | A | 1/1969 | Waters |
| 3,592,203 | A | 7/1971 | Johnson |
| 3,734,107 | A | 5/1973 | Thierman |
| 4,133,339 | A | 1/1979 | Naslund |
| 4,307,740 | A | 12/1981 | Florindez et al. |
| 4,920,993 | A | 5/1990 | Mackie |
| 5,020,554 | A | 6/1991 | Feinberg |
| 5,188,133 | A | 2/1993 | Romanus |
| 5,269,331 | A | 12/1993 | Tanriverdi |
| 5,482,466 | A | 1/1996 | Haynes |
| 5,678,578 | A | 10/1997 | Kossak et al. |
| 5,782,250 | A | 7/1998 | Harrah, Jr. |
| 5,816,271 | A | 10/1998 | Urso |
| 5,823,207 | A | 10/1998 | Bushman |
| 5,947,133 | A | 9/1999 | Kossak et al. |
| 6,092,536 | A | 7/2000 | Owens |
| 6,526,994 | B1 | 3/2003 | Santoro |
| 2004/0255972 | A1 | 12/2004 | Chen |

*Primary Examiner*—Robyn Doan
*Assistant Examiner*—Rachel A Running
(74) *Attorney, Agent, or Firm*—Cantor Colburn LLP

(57) ABSTRACT

A flossing device having internal floss feed in which floss is advanced from a storage chamber inside the handle of the device, through feed gears, to a pair of spaced apart tines. Spent floss is returned through the return gears, the return drive gear having a greater diameter than the feed drive gear, thus ensuring the floss remains taut between the tines. An integral cutter allows the spent floss to be cut off and discarded. The cover over one or both sets of gears may be open at the top and bottom to allow cleaning of the gears. A flexible tile may be included over the aperture through which the floss exits the storage chamber to prevent water incursion therein.

A floss advance lever advances the floss by a single action when pressed forward, which creates and maintains sufficient tensions on the floss resulting in taut and snug floss between the tines. Optionally, the flossing head has a vibratory device to aid in the flossing action.

16 Claims, 10 Drawing Sheets

100

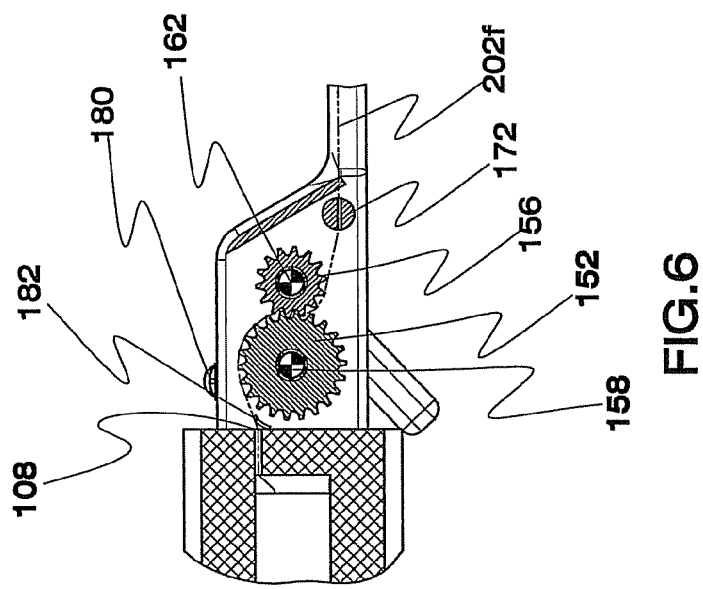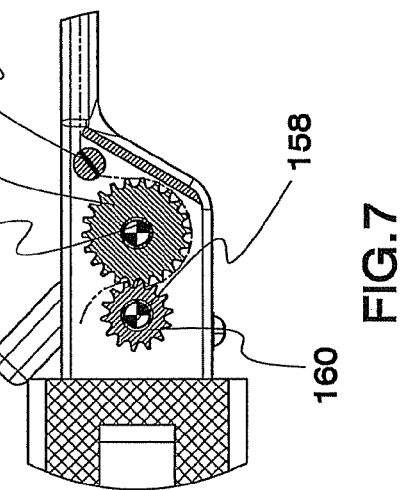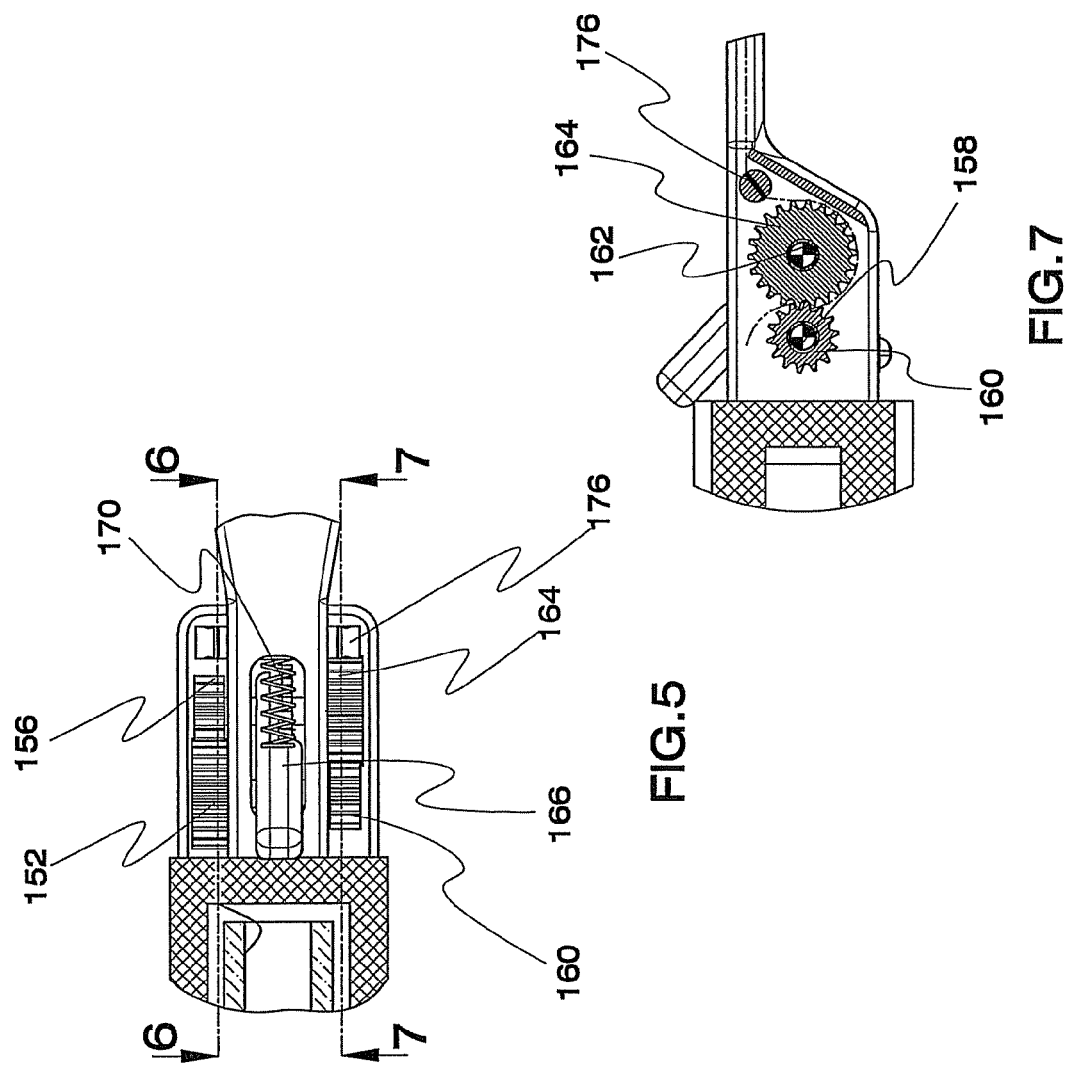

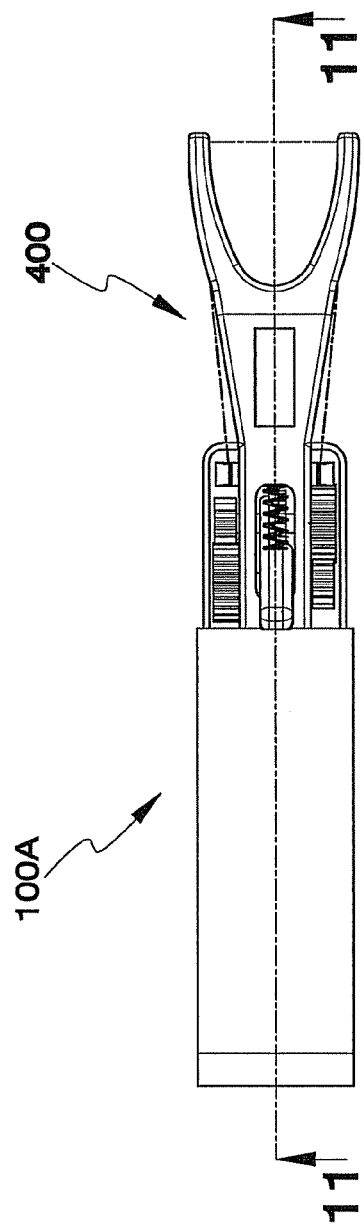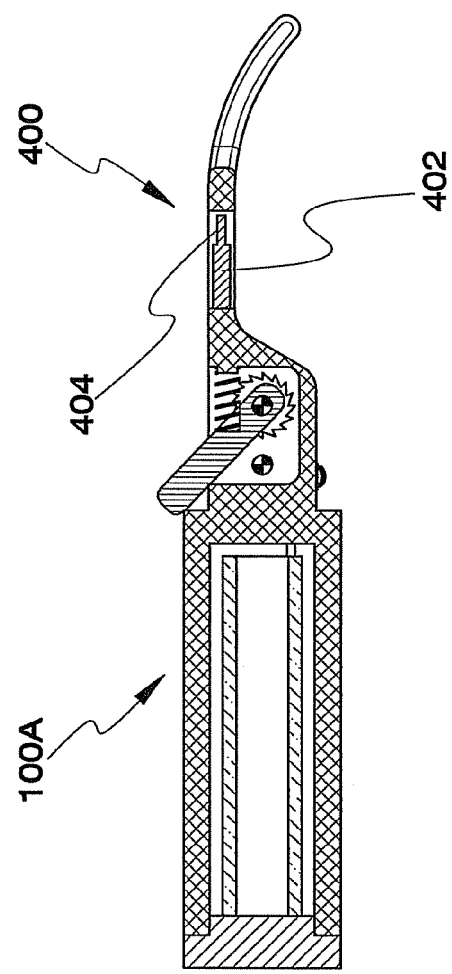
FIG.10
FIG.11

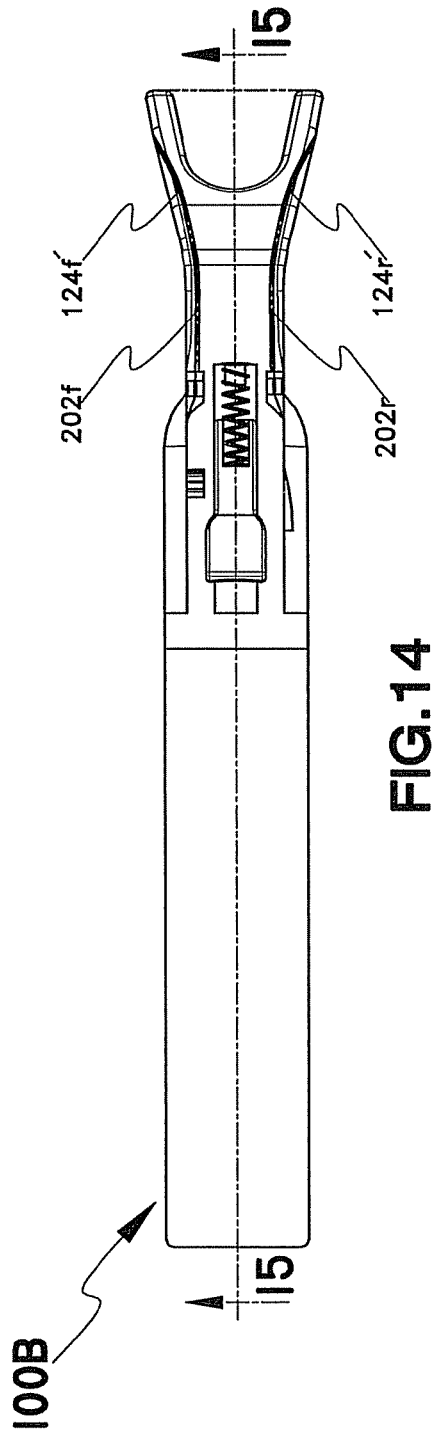
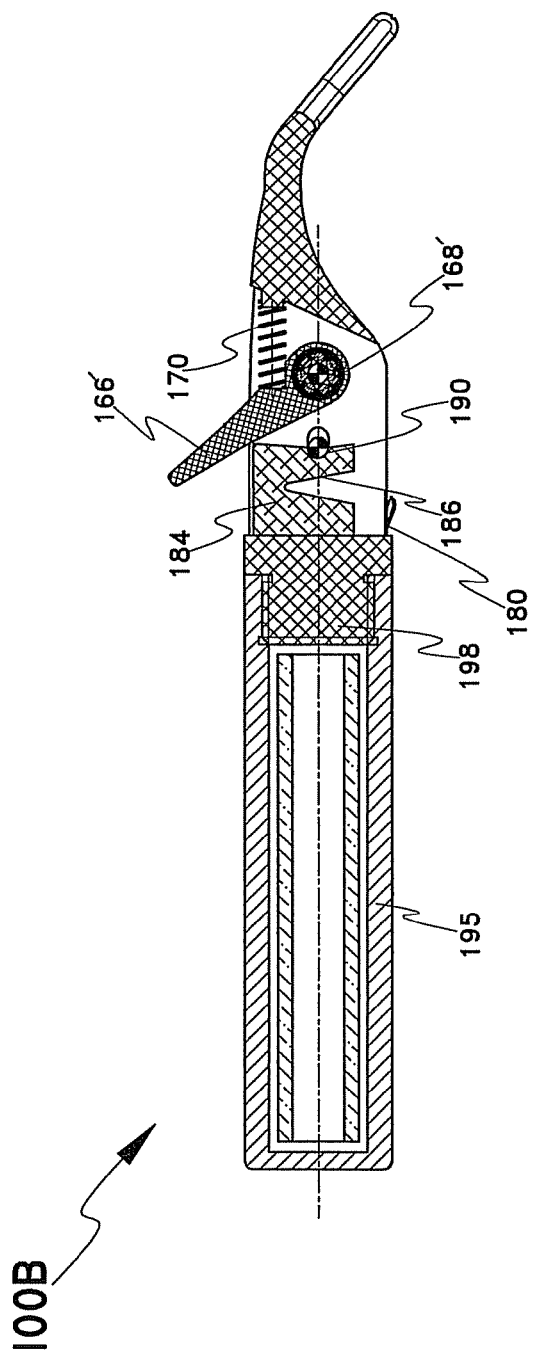

FLOSSING DEVICE WITH INTERNAL FLOSS FEED

RELATED APPLICATIONS

This application is a Continuation-In-Part of Ser. No. 10/846,575, filed May 17, 2004.

BACKGROUND OF THE INVENTION

1. Field of the Invention

The present invention relates to dental hygiene products. More particularly, the invention comprises a flossing device with internal storage of floss and an internal feed mechanism for progressing fresh floss through the flossing head.

2. Description of the Prior Art

Numerous flossing devices have been disclosed over the years, may with internal storage for the floss, and many of those with feed mechanisms for advancing the floss through the flossing tines.

Of particular note are U.S. Pat. No. 6,526,994 to Santoro on Mar. 4, 2003; U.S. Pat. No. 5,823,207 to Bushman on Oct. 20, 1998; U.S. Pat. No. 5,947,133 to Kossak, et al., on Sep. 7, 1999; U.S. Pat. No. 5,816,271 to Urso on Oct. 6, 1998; and U.S. Pat. No. 5,269,331 to Tanriverdi on Dec. 14, 1993.

In each case cited above, floss is fed from a supply spool through the tines and back to a take up spool, with all motivational forces being applied to the either the supply spool, the take up spool or both. In none of the above are the motivational forces applied directly to the floss, as in the present invention.

None of the above inventions and patents, taken either singly or in combination, is seen to describe the instant invention as claimed.

SUMMARY OF THE INVENTION

Dentists recommend regular flossing as one of the best ways to maintain dental hygiene and health. Many people, however, find the act of flossing clumsy and difficult. Flossing by hand requires stretching floss between the fingers of both hands and then working the fingers into the mouth, flossing a given area of the mouth, advancing the floss through the fingers and then flossing another area of the mouth. The advancing of the floss is important in order to prevent the spreading of germs and debris from one area of the mouth to another. By means of the internal mechanism provided by the present invention, the floss is easily refreshed by rotating the floss advance wheel.

The present invention provides flossing device which has a chamber within its hollow handle in which a spool of floss is stored. The free end of the floss is threaded through an array of feed gears to a pair of tines at the head of the device and back to the take up gears for take up. The floss is maintained taut between the tines of the head for effective flossing. In an alternative embodiment, an electrically operated vibrator is housed in the flossing head to aid in stimulating the gums and removal of dental debris.

Accordingly, it is a principal object of the invention to provide a flossing device that is easy to use.

It is another object of the invention to provide a flossing device which stores the floss internally.

It is a further object of the invention to provide a flossing device which is self cleaning.

Another object of the invention to provide a flossing device which can easily provide fresh floss for each tooth to be flossed.

It is, again, an object of the invention to provide a flossing device which maintains the floss in a taut state between the tines of the head for effective flossing.

Still another object of the invention to provide a flossing device which isolates clean floss from contaminated floss.

Still another object of the invention to provide a floss hollow chamber which is detachable for refilling purposes and water tight.

A further object of the invention to provide a flossing device which can easily be washed and cleaned after use without making the floss in the storage chamber wet or contaminated.

An additional object of the invention to provide a flossing device with vibratory action to aid in gum stimulation and removal of dental debris.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 5 is a partial top, partially cut-away view of the flosser of the present invention at 5 of FIG. 3.

FIG. 6 is a partial side, cut-away view of the left side of the flosser of the present invention at line 6-6 of FIG. 5

FIG. 7 is a partial side, cut-away view of the left side of the flosser of the present invention at line 7-7 of FIG. 5

FIG. 10 is a plan view of the flosser of the present invention with an oscillating head.

FIG. 11 is a side, cut-away view of the flosser of the present invention at line 11-11 of FIG. 10.

FIG. 14 is a top view of the alternative embodiment of the flosser of the present invention.

FIG. 15 is a cross-sectional side view of the alternative embodiment of the flosser of the present invention at lines 15-15 of FIG. 14.

DETAILED DESCRIPTION OF THE PREFERRED EMBODIMENTS

Figure 1:
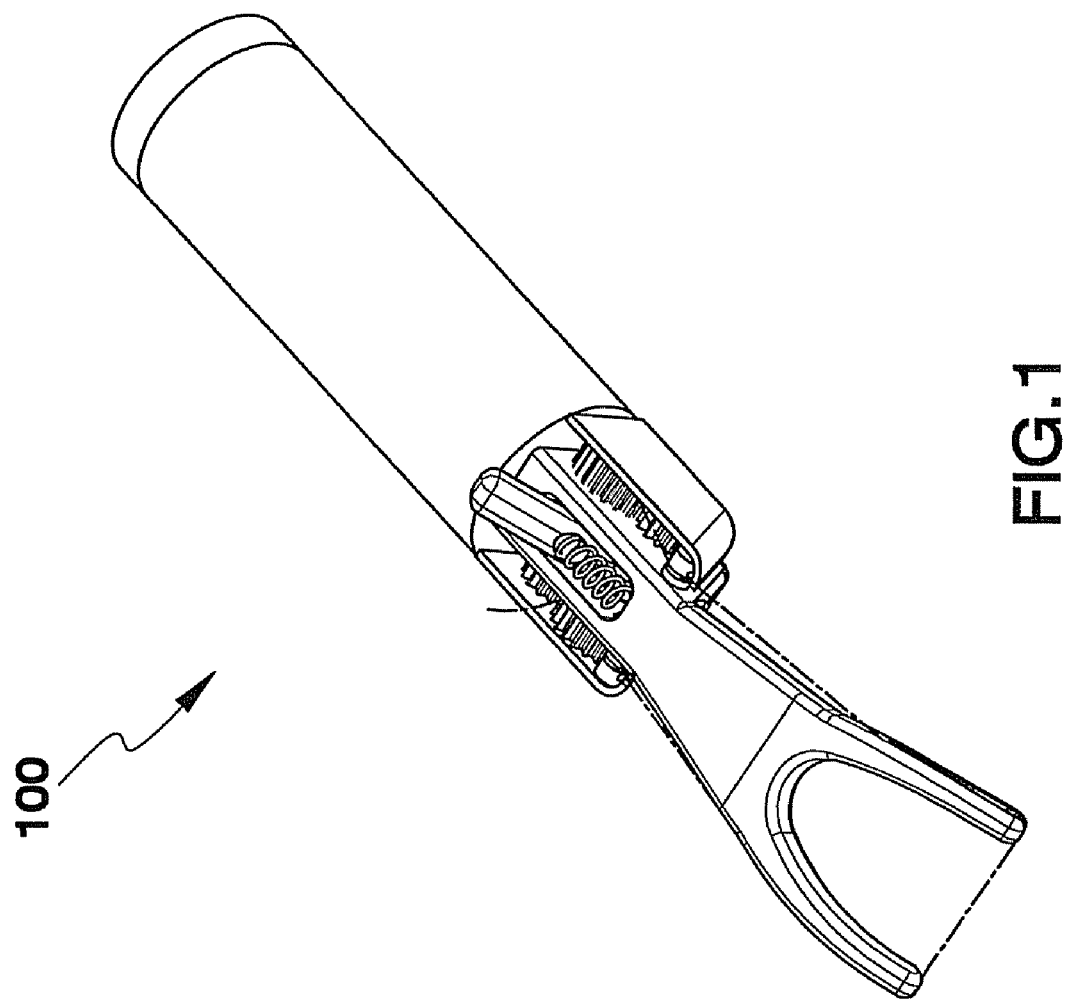
FIG. 1 is a top perspective view of the flosser of the present invention.
Figure 2:
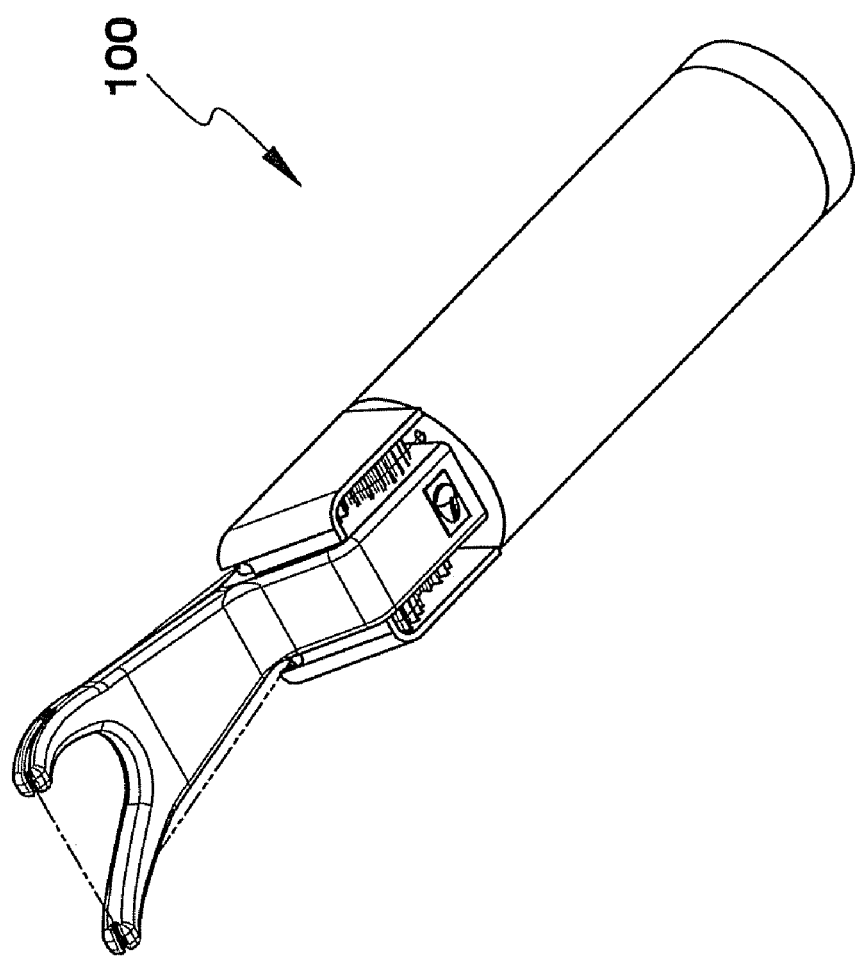
FIG. 2 is a bottom perspective view of the flosser of the present invention.

The flosser 100 of the present invention, as shown in its assembled state at FIGS. 1 and 2, is depicted in further detail at FIGS. 3 through 8.

The flosser 100 has a body 102 having a hollow handle portion 104 at a first end, handle portion 104 having a threaded cap 106 at a first end of handle portion 104 and a threading aperture 108 at a second end of handle 104. Handle 104 is dimensioned and configured to comfortably fit into a human hand.

At a second end of body 102 is a head 110, head 110 extending longitudinally from the second end of handle 104. Head 110 is solid and substantially flat on its upper and lower surfaces, and is dimensioned and configured for the free end of head 110 to comfortably fit within a human mouth. At the free end of head 110 is a pair of tines 112f and 112r which are angled downwardly from the free end of head 110 at an angle which allows easy access to the teeth. (In the preceding and hereinafter, the designation "f" behind a number will refer to the feed side of the flosser 100 and the designation "r" the return side.) Each of tines 112f and 112r has a groove 114f and 114r, respectively, formed at the end thereof, the groups 114f and 114r being substantially in a plane with one another. Tines 112f and 112r each have a guide groove 124f' and 124r', respectively, formed proximate the edge thereof to aid in guiding floss 202f and 202r along the length thereof.

Proximate the juncture with handle 104, head 110 floss feed assembly 150 mounted within and on the two opposing sides of head 110 proximate its juncture with handle 104. Interior of head 110 is a floss feed lever well 151 formed along the longitudinal axis of head 110 proximate its juncture with handle 104. (While floss feed lever 151 could be closed at the bottom, as illustrated, it could likewise be formed passing filly through head 110). The floss feed assembly 150 consists of a floss feed gear 152 rotatably mounted at a first end of an axle pin 158, which is mounted through head 10 and floss feed lever well 151 and substantially normal thereto. A return gear 160 is, likewise, rotatably mounted at the second end of axle pin 158, feed gear 152, and return gear 160 being on opposite sides of head 110.

A feed drive gear 156 is rigidly mounted at a first end of a drive axle pin 62, which is mounted through head 110 and floss feed lever well 151, substantially normal thereto. A return drive gear 164 is, likewise, rigidly mounted at the second end of drive axle pin 162.

Axle pin 158 and drive axle pin 162 are positioned and feed gear 152 and return gear 160 and feed drive gear 156 and return drive gear 164 are dimensioned such that feed gear 152 engages feed drive gear 156 snugly, and the return drive gear 164 engages return gear 160 snugly.

A floss advance lever 166 has a first, free end and a second attachment end. An aperture 165 is formed through the floss advance lever 166 proximate the attachment end. Drive axle pin 162 passes through aperture 165 of floss advance lever 166, within floss advance lever well 151, thereby allowing floss advance lever 166 to rotatably engage drive axle pin 162. A ratchet gear 168 is fixedly attached to drive axle pin 162 at a point within floss advance lever well 151 at a point adjacent to floss advance lever 166, and a ratchet engagement member 167 is attached to the side of floss advance lever 166 such that an end of ratchet engagement member 167 engages ratchet gear 168. The engagement of ratchet gear 168 and ratchet engagement member 167 allows the floss advance lever 166 to rotate the drive axle pin 162 on a forward stroke of floss advance lever 166 and move freely on the back stroke of floss advance lever 166, thereby rotating feed drive gear 156 and return drive gear 164 in only one direction. A compression spring 170 returns the floss advance lever to the rearward position automatically.

A feed capstan 172 and a return capstan 176 are situated between feed drive gear 156 and return drive gear 164 and tines 112f and 112r, respectively, thereby aiding in guiding the floss 202 as it passes between the feed drive gear 156 and return gear 164 and the grooves 124f' and 124r' of tines 112f and 112r, respectively. Grooves 172a and 176a around the perimeters of capstans 172 and 176, respectively, retain the floss 202f and 202r on the capstans 172 and 176. Feed assembly housings 116f and 116r enclose the feed and return sides of feed assembly 150, respectively. It is preferable that feed assembly housing caps 116f and 116r leave the top and bottom of the feed assembly open to aid in the rinsing of the feed assembly 150 with running water.

A floss cutter 180, as is typically found on floss dispensers, is mounted on the lower surface of head 110.

A light weight, flexible tile 182, configured to conform to the face of the juncture wall between hollow handle 104 and head 110, aids in preventing water from infiltrating the interior of handle 104 through the threading aperture 108 during washing. Tile 182 has sufficient flexibility to allow the floss to easily pass through the threading aperture 108, while still conforming to the surface of the wall around threading aperture 108.

In a second embodiment of the flosser 100A (FIGS. 10 and 11), a vibrator 400 may be added to the head 110 of flosser 100A. Vibrator 400 consists of a motor 402 with an eccentric head 404. Motor 400 is powered by an electrical cord (not shown) or battery (not shown) housed in the hollow handle 104. The vibration of vibrator 400 provides improved stimulation of the gums and cleaning of the teeth over the flosser 100, without the vibrator 400.

Figure 9:
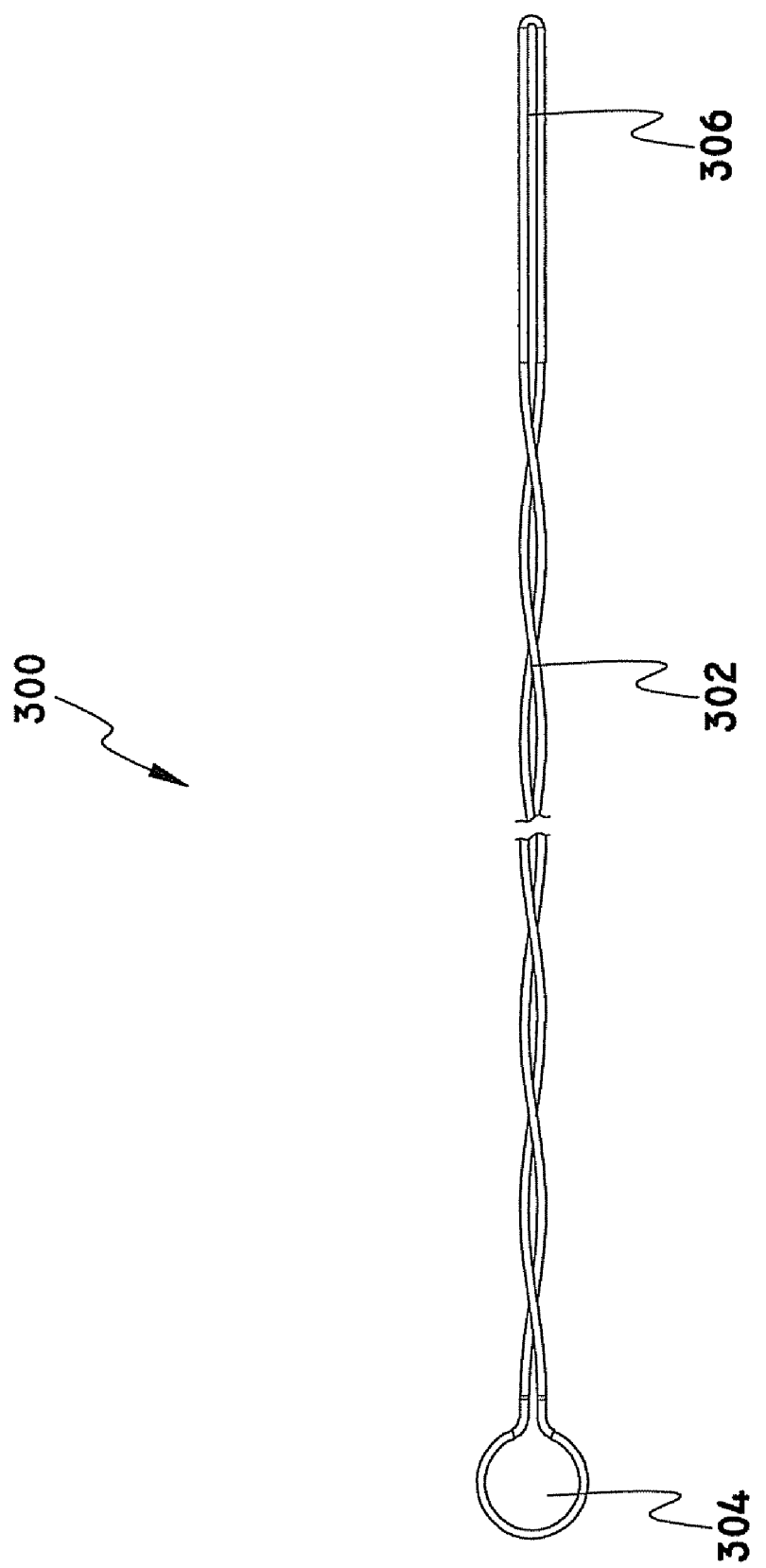
FIG. 9 is a side view of the threading tool of the flosser of the present invention.

A threading needle 300 (FIG. 9) is provided to aid in the threading of floss through the threading aperture 108 of handle 104. Threading needle 300 has a shaft 302 which may be inserted through threading aperture 108 of head 110, and extended out the end of handle 104. A finger ring 304 is at a first end of the shaft 302 and an eye 306 at the second end. The end of a floss 202 form a spool 200 may be threaded through the eye 306 of needle 300 before withdrawing needle 300 from threading aperture 108. The floss 202 is then threaded through the flosser 100, as further defined hereinbelow.

Figure 3:
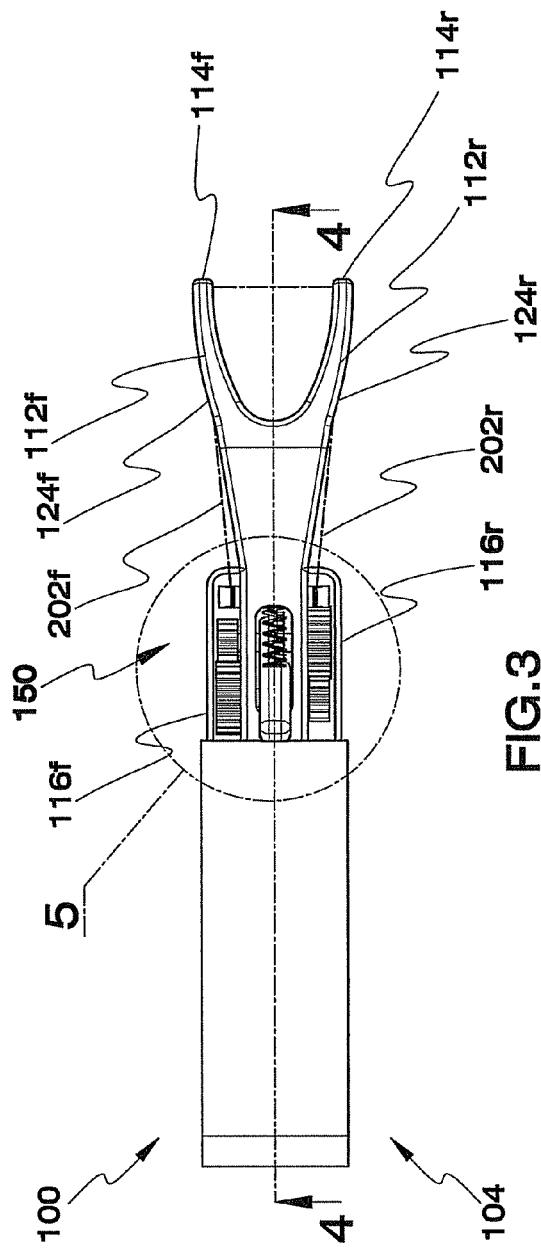
FIG. 3 is a top view of the flosser of the present invention.
Figure 4:
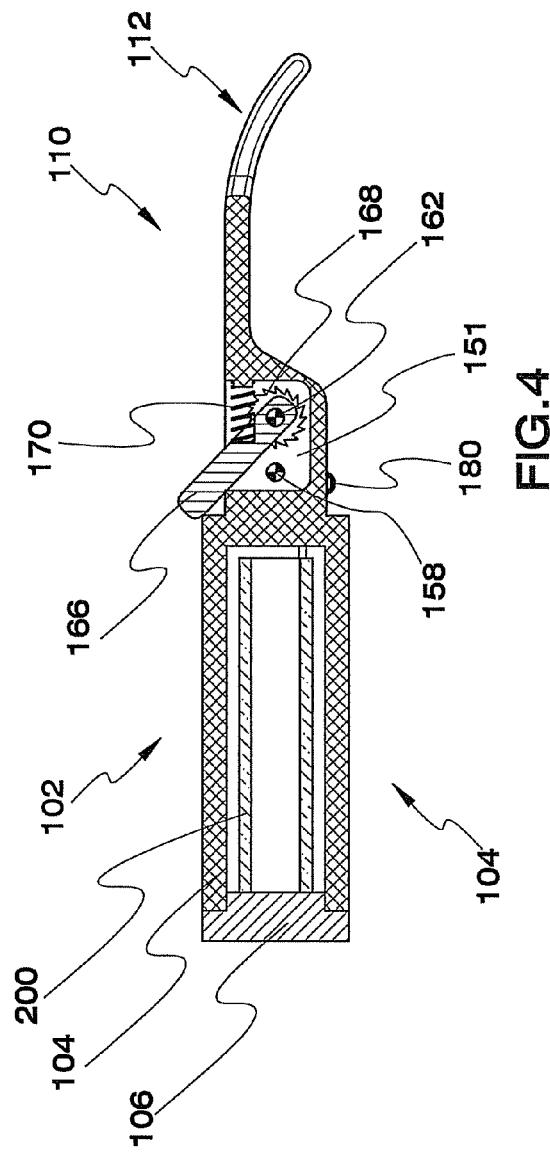
FIG. 4 is a cross-sectional side view of the flosser of the present invention at line 4-4 of FIG. 3.
Figure 8:
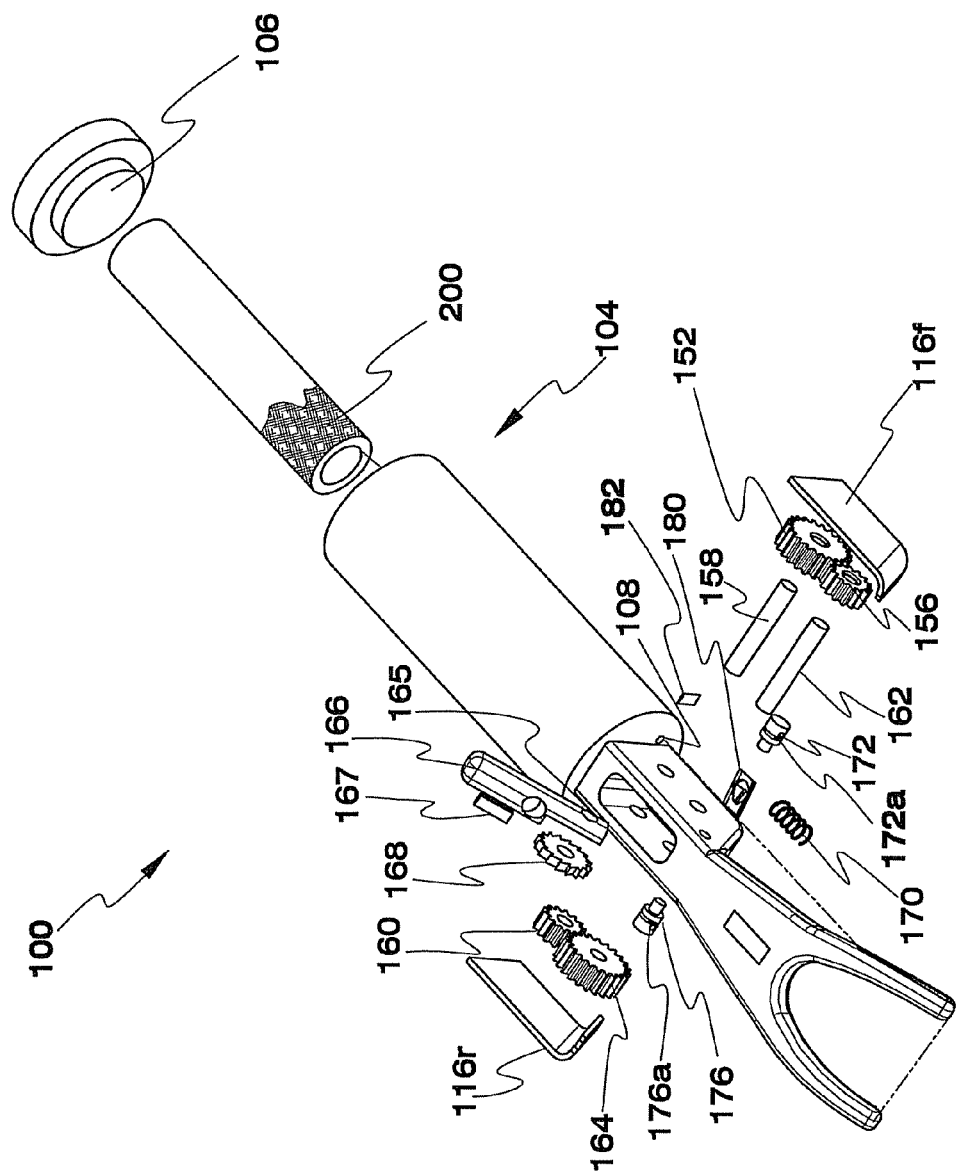
FIG. 8 is an exploded top perspective view of the flosser of the present invention.

Referring now to FIGS. 3, 5, and 6, floss 202 from a spool 200 is fed through threaded aperture 108 to the floss feed assembly 150, using needle 300. The end of the floss 202 is then fed through feed gear 152 and feed drive gear 156, then into the groove 172a around feed capstan 172. The floss 202 is then fed along the guide groove 124f becoming floss 202f of a first tine 112f, through the tine groove 114f of the same tine 112f, and then through the tine groove 114r of the second tine 112r becoming 202r (In use, the floss 202f between the tines 112 becomes soiled with food debris, therefore, hereinafter, the soiled floss will be referred to as floss 202r, soiled floss being returned to the floss feed assembly 150.) The floss 202r is then fed through guide groove 124r and back to the floss feed assembly 150, where it passes between the return drive gear 164 and return gear 160 before passing to the floss cutter 180, where spent floss 202r may be cut off.

Return drive gear 164 has a larger diameter than does feed drive gear 156, thereby ensuring that the floss 202 is constantly under tension, preventing slack in the floss 202 between the tines 112. It should be noted that clean floss 202f and soiled floss 202r travel through different channels throughout the system. Floss is fed through the floss feed assembly 150 by ratcheting the floss advance lever 166 forward.

In use, the tines 112 of the flosser 100 should be placed within the mouth, with the floss 202 passing into the gap between two adjacent teeth. After flossing between the two teeth, the flosser 100 should be removed from the mouth and the floss 202 advanced between the tines 112 by ratcheting floss advance lever 166. This action should be repeated after flossing each pair of adjacent teeth. The used floss 202 may be periodically cut by cutter 180. After flossing, the floss feed assembly 150 should be cleaned by rinsing with running water, and the flosser 100 left to dry.

Following is a description of an alternative embodiment of the flosser of the invention. In FIGS. 12-15, which show this alternative embodiment, all elements having the same reference numerals used in the embodiment of FIGS. 1-11 should be understood to have the same function as they served in that embodiment. Numerals followed by (') indicate cosmetic, minor modification or change in function. New numbers indicate a new part.

Figure 12:
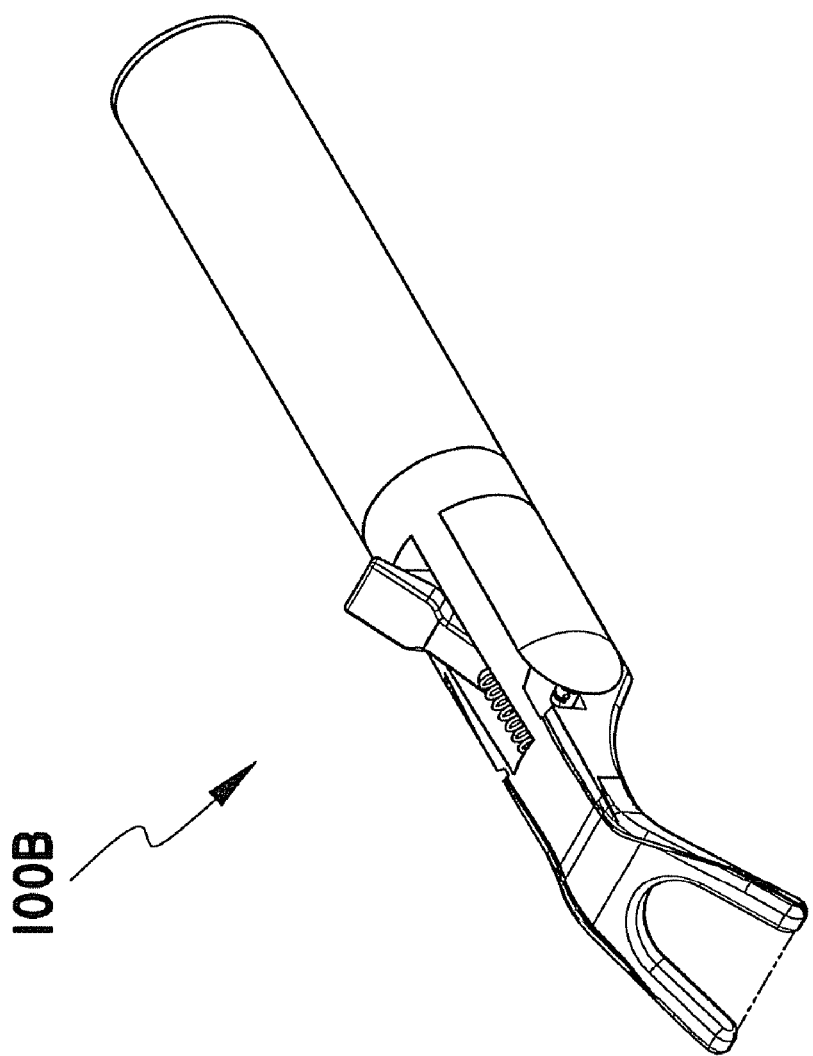
FIG. 12 is a top perspective view of an alternative embodiment of the flosser of the present invention.
Figure 13:
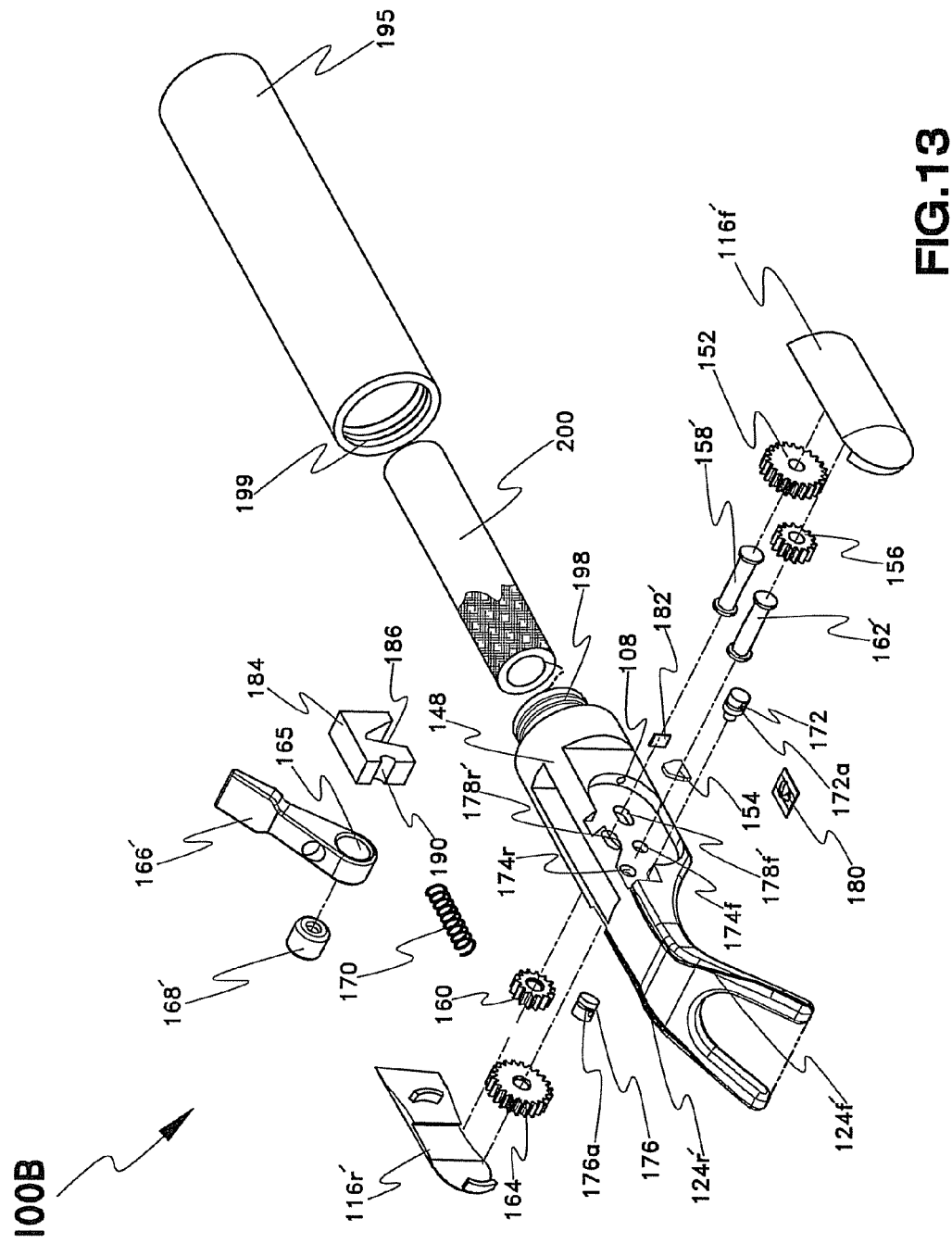
FIG. 13 is an exploded top perspective view of the alternative embodiment of the flosser of the present invention.

FIG. 12 shows a top perspective view of the alternative embodiment 100B of the flosser. As can be seen in FIG. 13, 198 and 199 are male and female threads, respectively, which allow floss housing 195 and flosser body 148 to be releasably secured together by screw motion to enable refilling the floss 200 within housing 195. Tensioner 184 is a plastic or metal part which functions as a spring, pushing forward the axle pin 158' within the oval axle pin apertures 178r' and 178f' resulting in tight engagement of feed drive gear 152 and feed gear 156 as well as return drive gear 164 and return gear 160, respectively. Axle pin drive apertures 174r and 174f and drive axle pin 162' are circular in shape, with apertures 174r and 174f rotatably accommodating ends of the drive axle pin 162' therein. Axle pin apertures 178r' and 178f' are oval shaped, leaving slack which allows tensioner 184 to press axle pin 158' towards the axle drive pin 162', thereby engaging said gears tightly. This snug arrangement thereby compensates for manufacturing deformities, eccentricness, and wear of the gears and also doesn't allow slipping of floss 200 routed along said gear engagements. A groove 186 is provided on the underside of tensioner 184, allowing the tensioner to compress when placed in position and expand consequently affecting spring action. The axle groove 190 function is retaining the tensioner 184 in the right position relative to the axle pin 158'. A feed capstan 172 and the feed groove 172a are used to guide the floss 202f from the feed drive gear 156 and feed gear 152 towards the groove 124f'. A return capstan 176 and return groove 176a are used to guide the floss 202r from the return groove 124r' towards the return drive gear 164 and return gear 160. A threading aperture 108 allows floss 202f to pass between hollow handle 195 and flosser body 148.

A plastic flexible tile 182', configured to cover and seal tightly the aperture 108, aids in preventing water from infiltrating the interior of handle 195 through the threading aperture 108 during washing. Flexible tile 182' has sufficient flexibility to allow the floss 202f to easily pass through the threading aperture 108, while sealing tightly the end of aperture 108. Guiding capstan 154 grips floss as the floss is passing through its narrow and flexible slot and prevents the floss from becoming loose and disengaging from position between gears.

Advance lever 166' fixedly and rigidly houses the outer surface of the outer casing of ratchet engagement member 168' in aperture 165 of advance lever 166'. The ratchet engagement member 168' is a clutch bearing, as known in the art, functioning in a manner that allows only a ratcheting rotation in one direction. The ratchet engagement member 168' grips the drive axle 162' ratchetably. By gripping the hollow handle 195 between the thumb and fingers of a human hand and pushing forward the advance lever 166', the drive axle 162' will rotate in a forward direction resulting in advancing the floss and creating tension in the floss between the feed drive gear 156 and return drive gear 164 simultaneously. The advance lever 166' will return to its first position by force of the helical spring 170, as shown in FIG. 15, when released. The feed assembly housing cap 116f', and return assembly housing cap 116r' have been designed in order to protect the hands of the user and the feed and return assembly housing caps are easily removable for purposes of cleaning the gears and/or refilling the spool of floss 200. Feed assembly housing cap 116f' is open at the bottom and the top allowing the user to rinse the soiled area of return drive gear 160 and 164 which contacts used portion of floss on return cycle. Return assembly housing cap 116r' can also be opened at the top and bottom, if so desired. The push advance lever 166' has been designed with an ergonomic shape. Flosser 100B further includes a cutter 180 to cut spent portions of the floss. The cutter is of similar nature and similar position to that shown in FIG. 8. The floss 202f and 202r are routed through the flosser 100B in a manner corresponding to that described above in reference to the first flosser embodiment 100. The flosser 100B alternatively can be equipped with vibrating mechanism corresponding to that described above in reference to the first flosser embodiment 100A.

It is to be understood that the present invention is not limited to the embodiments described above, but encompasses any and all embodiments within the scope of the following claims.

The invention claimed is:

1. A flossing device with internal floss feed, comprising:
a body having a handle adapted for gripping with the human hand and a flossing head, an end of which is adapted for insertion into the human mouth,
storage means for storing a spool from which floss is discharged,
feed means for feeding said floss to said flossing head,
spanning means for spanning said floss between two points on said flossing head, said spanning means size for insertion of said floss between the teeth of a user,
return means for returning a used portion of said floss from said flossing head,
advance means for advancing said floss through said feeding means and said return means, and
housing means for housing said feed means and said return means;
wherein said feed means comprises a feed gear rigidly affixed to a first end of an axle pin rotatably mounted through a portion of said flossing head and a feed drive gear rigidly affixed to a first end of a drive axle pin rotatably mounted through said flossing head and in interconnecting, geared juxtaposition with said feed gear, whereby floss can pass between said feed gear and said feed drive gear only by advancing said feed gear and said feed drive gear, such that said floss is pulled from said spool and advanced beyond said feed gear and said feed drive gear, and
a feed capstan for guiding said floss from said feed means.

2. A flossing device with internal floss feed, as defined in claim 1, wherein said spanning means comprises a pair of tines at an end of said flossing head at a distance from said handle, each tine having a free end, a first one of said tines having a guide groove for guiding said floss from said feed means to said free end of said first tine, a tine groove at said free end of each of said tines for guiding said floss from said first tine to the second of said tines, and a second guide groove in said second tine for guiding said floss from said second tine to said return means.

3. A flossing device with internal floss feed, as defined in claim 1, wherein said return means comprises a return capstan for guiding said floss from said second tine to a return drive gear rigidly affixed to a second end of said drive axle pin and a return gear rotatably affixed to a second end of said axle pin, said return drive gear having a diameter greater than that of said feed drive gear, resulting in said floss being kept in a taut state between said tines, and said return drive gear in interconnecting, geared juxtaposition with said return drive gear, said floss intended to pass between said return drive gear and said return gear such that said floss is pulled from said tines and advanced beyond said return drive gear and said return gear.

4. A flossing device with internal floss feed, as defined in claim 3, wherein said advance means comprises a floss advance lever rotatably and ratchetingly affixed to said drive axle pin, by means of a clutch bearing which provides ratchet engagement,
- a spring adapted to return said floss advance lever to a stored position,
- said floss advance lever advancing said feed drive gear and said return drive gear, said feed drive gear and said return drive gear, in turn, driving said feed gear and said return gear.

5. A flossing device with internal floss feed, as defined in claim 3, wherein said advance means comprises a floss advance lever fixedly housing a clutch bearing, said clutch bearing rotatably and ratchetingly gripping the drive axle pin, thereby allowing said floss advance lever to advance said feed drive gear and said return drive gear in only one direction, wherein said floss advance lever advancing said feed drive gear and said return drive gear causes said feed drive gear and said return drive gear, in turn, to drive said feed gear and said return gear.

6. A flossing device with internal floss feed, as defined in claim 1, wherein said flossing head further comprises vibratory means for aiding in stimulating the gums and removing dental debris.

7. A flossing device with internal floss feed, as defined in claim 6, wherein said vibratory means comprises a motor and an eccentric head.

8. A flossing device with internal floss feed, as defined in claim 7, wherein said motor is powered by a battery internal of said flossing device.

9. A flossing device with internal floss feed, as defined in claim 7, wherein said motor is powered by an electrical cord and plug for connection to an external power supply.

10. A flossing device with internal floss feed, as defined in claim 1, further including threading means, said threading means comprising:
- a needle having a shaft, a finger ring at a first end of said shaft and an eye at a second end of said shaft, said shaft being adapted to be placed through said threading aperture and through said hollow compartment,
- said eye being adapted to receive an end of said floss for pulling said floss through said hollow compartment and said threading aperture.

11. A flossing device with internal floss feed, as defined in claim 1, further including cutting means comprising a floss cutter affixed to said flossing device.

12. A flossing device with internal floss feed, as defined in claim 1, wherein said storage means comprises a hollow compartment within said handle for holding a spool of said floss, said hollow compartment having a threaded female end which allows said hollow compartment handle to thread securely to male threads located on said flosser body, thereby removably sealing the end of said hollow compartment and making the floss housing detachable from the flosser body for floss refilling purposes.

13. A flossing device with internal floss feed, as defined in claim 1, wherein said axle pin is rotatably supported at two points thereof within two oval shaped apertures, said apertures oriented to allow said axle pin to slide within said apertures along a limited path that they define, said path being substantially normal to both a longitudinal axis of said drive axle pin and a longitudinal axis of said axle pin.

14. A flossing device with internal floss feed, as defined in claim 13, further comprising a tensioner device, said tensioner device having a spring-like function which, when in place within the flossing device, applies forwarding pressure on the axle pin, moving it forward in the oval shaped axle apertures, resulting in a tight engagement between said feed gear and said feed drive gear, and simultaneously between said return gear and said return drive gear, thus preventing the floss from slipping between each of the two geared juxtapositions, maintaining floss tautness between the tines, and compensating for any eccentricness and wear of the gears.

15. A flossing device with internal floss feed, comprising:
- a body having a handle adapted for gripping with the human hand and a flossing head, an end of which is adapted for insertion into the human mouth,
- storage means for storing a spool from which floss is discharged,
- feed means for feeding said floss to said flossing head,
- spanning means for spanning said floss between two points on said flossing head, said spanning means sized for insertion of said floss between the teeth of a user,
- return means for returning a used portion of said floss from said flossing head,
- advance means for advancing said floss through said feeding means and said return means,
- housing means for housing said feed means and said return means, and
- wherein said housing means comprises two removably affixed covers enclosing said feed means and said return means, respectively,
- said cover enclosing said return means being open at a top and bottom thereof, thereby aiding in cleansing of said return means.

16. A flossing device with internal floss feed comprising:
- a body having at a first end thereof a handle adapted for gripping with the human hand and a flossing head located at a second end of said body, said flossing head being adapted for insertion into the human mouth,
- storage means for storing a spool from which floss is discharged,
- feed means for feeding said floss to said flossing head,
- spanning means for spanning said floss between two points on said flossing head, said spanning means sized for insertion of said floss between the teeth of a user,
- return means for returning a used portion of said floss from said flossing head,
- advance means for advancing said floss through said feeding means and said return means,
- housing means for housing said feed means and said return means, and
- wherein said storage means comprises a hollow compartment within said handle for holding a spool of floss, said handle being threadingly attached to said first end of said body, whereby said body forms an end wall of said compartment and makes said compartment watertight while allowing refilling of a spool of floss therein, said storage means further comprising a threading aperture for allowing passage of said floss from within said compartment to said feed means, further comprising sealing means for sealing said storage means from intrusion of water during cleaning of said flossing device, said sealing means comprising a flexible tile located at the end of said housing means and against the portion of the hollow compartment of the handle containing said threading aperture, to prevent infiltration of water into said hollow chamber during washing of said flossing device.

* * * * *